United States Patent
Handa et al.

(10) Patent No.: US 6,235,896 B1
(45) Date of Patent: May 22, 2001

(54) PROCESS FOR THE PREPARATION OF CEFUROXIME

(75) Inventors: Vijay Kumar Handa; Ramesh Dandala, both of New Delhi; Jag Mohan Khanna, Gurgaon, all of (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 09/264,977

(22) Filed: Mar. 9, 1999

(30) Foreign Application Priority Data

Mar. 30, 1998 (IN) .............................................. 818/DEL/98

(51) Int. Cl.$^7$ ................................................ C07D 501/34
(52) U.S. Cl. ............................................................ 540/222
(58) Field of Search ............................................... 540/222

(56) References Cited

U.S. PATENT DOCUMENTS

| 3,966,717 | 6/1976 | Cook et al. | 424/246 |
| 3,974,153 | 8/1976 | Cook et al. | 424/246 |
| 4,138,555 | 2/1979 | Cook et al. | 544/16 |
| 4,258,183 | 3/1981 | Humber et al. | 544/21 |
| 4,775,750 * | 10/1988 | White | 540/222 |
| 5,063,224 | 11/1991 | Mosher et al. | 514/202 |

FOREIGN PATENT DOCUMENTS

| 1027554 | 3/1978 | (CA) . |
| 1027933 | 3/1978 | (CA) . |
| 1342241 | 1/1970 | (GB) . |
| 1571683 | 2/1976 | (GB) . |

* cited by examiner

Primary Examiner—Mark L. Berch
(74) Attorney, Agent, or Firm—Jayadeep R. Deshmukh, Esq.

(57) ABSTRACT

There is described a process for the preparation of cefuroxime from predominantly S-cefuroxime axetil, R, S mixture of cefuroxime axetil or R-cefuroxime axetil not meeting the purity criteria. This comprises treating cefuroxime axetil with alkoxides in the presence of a suitable solvent or solvent mixture and isolating cefuroxime from the reaction mixture.

13 Claims, No Drawings

PROCESS FOR THE PREPARATION OF CEFUROXIME

FIELD OF THE INVENTION

The present invention is directed generally to a process for the preparation of cefuroxime axetil and more specifically to such a process, the starting ingredient being one of predominantly S-cefuroxime axetil, R,S mixture of cefuroxime axetil or R-cefuroxime axetil not meeting the purity criteria.

BACKGROUND OF THE INVENTION

Cefuroxime is a cephalosporin antibiotic with a broad spectrum of activity against both gram-positive and gram-negative microorganisms. Due to poor absorption from the gastrointestinal tract following oral administration, its salt, cefuroxime sodium, is ideally suited to formulation as injectables. The need for a more convenient and broader therapeutic use of cefuroxime led to the synthesis of 1-acetoxyethyl ester of cefuroxime, which is referred to as cefuroxime axetil. Cefuroxime axetil is a prodrug of cefuroxime and is suitable for oral administration. As a result, it permits a more convenient and broader therapeutic use of cefuroxime.

Cefuroxime axetil possesses an asymmetric carbon atom at the 1-position of the 1-acetoxyethyl group and, therefore, can exist as R- and S-isomers and mixtures thereof. Cefuroxime axetil is marketed as a mixture of R- and S-isomers in an approximately 1:1 ratio.

While cefuroxime axetil well suited to formulation for oral administration, it suffers from several deficiencies. Cefuroxime axetil is rapidly hydrolyzed in the intestine, thereby resulting in the formation of cefuroxime, which is poorly absorbed from the gastrointestinal tract. It has also been observed that oral administration of the R,S-mixture results in only about 50% bioavailability of the cefuroxime antibiotic, which is due to low overall solubility and the rapid hydrolysis of the ester portion of cefuroxime axetil by the esterase enzyme located in the gut. The non-absorbable cefuroxime remaining in the gut accounts for a partial loss of therapeutic activity and possibly the cause of side effects generally observed.

The rate of cleavage of ester group of the individual R- and S-isomers of cefuroxime axetil by esterase enzyme is different and it has been discovered that the individual S-isomer is hydrolyzed in animals much more rapidly than the R-isomer. U.S. Pat. No. 5,063,224 provides a process for preparing substantially pure R-cefuroxime axetil. It embodies the invention by claiming the superior stability to esterases and greater bioavailability of R-cefuroxime axetil over S-isomer, thus reducing the amount of non-absorbable cefuroxime remaining in the gut lumen, thereby diminishing the side effects attributable to cefuroxime. However, said patent does not describe the use of the undesirable S-isomer. Accordingly, there has been a need for a process whereby the undesirable S-isomer could be recycled. Such a process would not only be useful in minimizing the waste should R-cefuroxime axetil be used as a drug, but also be advantageous from a commercial standpoint.

SUMMARY OF THE INVENTION

An object of the present invention is to provide a process for the preparation of cefuroxime from predominantly S-cefuroxime axetil, R, S mixture of cefuroxime axetil or R-cefuroxime axetil not meeting the purity criteria.

The present invention provides a process for the conversion of cefuroxime axetil as seen in Formula I as follows:

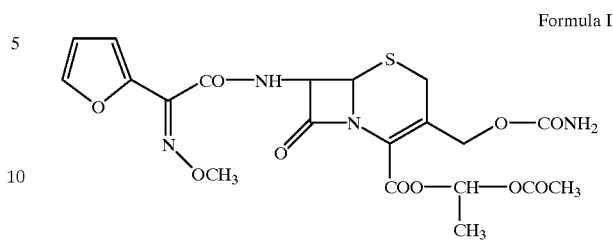

Formula I into cefuroxime as seen in Formula II as follows:

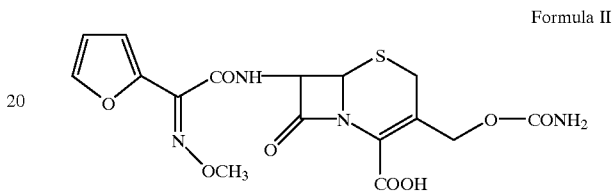

Formula II which comprises treating cefuroxime axetil with alkoxides in the presence of a suitable solvent(s) as described herein and isolating cefuroxime from the reaction mixture. The reaction is carried out at a temperature ranging from approximately −80 to +40° C., most preferably at approximately −65 to +20° C. After completion of the reaction, aqueous hydrochloric acid is added to the reaction mixture, the solvent is removed under reduced pressure and water is added to the reaction mixture. Cefuroxime is extracted with a water-immiscible solvent. A basifying agent is added and cefuroxime is precipitated from the aqueous layer by acidification.

The term "suitable solvent(s)" denotes any lower alkanol or non-alcoholic polar solvent(s) and mixture thereof, which is capable of homogenizing the reaction mixture. The lower alkanol includes those primary, secondary and tertiary alcohols having from one to six carbon atoms. Preferably, the lower alkanol solvents used are methyl, ethyl and isopropyl alcohol. The non-alcoholic polar solvents include tetrahydrofuran, 1,4-dioxane, N,N-dimethylformamide and dimethylsulfoxide. Preferably, tetrahydrofuran and 1,4-dioxane are used. Mixtures of two or more lower alkanols and/or other non-alcoholic polar solvents can also be used.

Any alkali alkoxides may be used, however, sodium alkoxides, such as sodium methoxide and sodium ethoxide, which are commercially available, are preferred. Any water-immiscible solvent may be used for extraction purposes, however, keeping in mind commercial availability and cost benefits, it is preferred that the solvent be selected from the group consisting of ethyl acetate, ether or dichloromethane.

The cefuroxime prepared according to the present invention may be converted into cefuroxime axetil or cefuroxime sodium by methods known per se.

The present invention is further illustrated by the following examples, none of which should be construed as limiting the scope of this invention in any way.

DETAILED DESCRIPTION OF THE INVENTION

EXAMPLE 1

Sodium metal (1.8 gm) was reacted under nitrogen atmosphere with ethyl alcohol (40 ml) at room temperature, resulting in a clear solution of sodium ethoxide. A solution of cefuroxime axetil (20.4 gm, S-isomer >90%, R-isomer <10%) in a mixture of tetrahydrofuran (204 ml) and ethyl alcohol (20 ml) was cooled to −60° C. A solution of sodium ethoxide in ethanol was slowly added to this mixture at −60° C. Progress of the reaction was monitored by high pressure liquid chromatography (HPLC). Stirring was continued until cefuroxime axetil almost disappeared (45 minutes). Thereafter, 15% aqueous hydrochloric acid (20 ml) was added and the solvent was evaporated under reduced pressure at low temperature. Water and ethyl acetate (water-immiscible solvent) were added to the reaction mass (basifying agent) and the pH level was adjusted to 6.0 using 5% aqueous potassium bicarbonate solution. The aqueous layer was separated and acidified with 15% aqueous hydrochloric acid to pH 1.0. The resulting solid was filtered, washed with water and dried to yield cefuroxime (15.2 gm).

EXAMPLE 2

To a solution of cefuroxime axetil (20.4 gm, S-isomer >90%, R-isomer <10%) in a mixture of tetrahydrofuran (204 ml) and methanol (14 ml) maintained at −60° C. was added freshly prepared sodium methoxide (1.89 gm, sodium metal was reacted in 28 ml methanol). The reaction contents were stirred for 1 hour and 15% aqueous hydrochloric acid (17 ml) was added. The solvent was distilled at low temperature under vacuum and water was added to the remaining reaction mass. Ethyl acetate was added and the pH level was adjusted to 6.0 with aqueous potassium bicarbonate. The aqueous layer was separated and acidified to pH 1.0 with aqueous hydrochloric acid. The separated solid was filtered, washed with water and dried to yield cefuroxime (15.66 gm).

EXAMPLE 3

Cefuroxime axetil (20.4 gm, predominantly S-isomer) was dissolved in a mixture of tetrahydrofuran (204 ml) and ethyl alcohol (58 ml). The solution was cooled to −60° C., sodium ethoxide (6.59 gm) was added in portions and the reaction mixture was stirred for 1 hour. Aqueous hydrochloric acid was added and the procedure described in Example 1 was followed to obtain cefuroxime (15.67 gm).

EXAMPLE 4

Cefuroxime axetil (20.4 gm, S-isomer >90%, R-isomer <10%) was dissolved in a mixture of tetrahydrofuran (204 ml) and methanol (39 ml). This clear solution was cooled to -60° C., and sodium methoxide (5 gm) was added. The reaction mixture was stirred at −55 to −60° C. for 1 hour. Hydrochloric acid was added and the procedure described in Example 2 was followed to obtain cefuroxime (15.19 gm).

EXAMPLE 5

(R,S) Cefuroxime axetil (20.4 gm, R and S isomers approximately 1:1 ratio) was converted into cefuroxime according to the method described in Example 4. Yield: 15.0gm.

While the present invention has been described in terms of its specific embodiments, certain modifications and equivalents will be apparent to those skilled in the art and are intended to be included within the scope of the present invention, which is to be limited only by scope of the appended claims.

What is claimed is:

1. The process for the preparation of cefuroxime (Formula II) from cefuroxime axetil of (Formula I), which comprises treating cefuroxime axetil with an alkoxide in the presence of a suitable solvent or solvent mixture and isolating cefuroxime from the reaction mixture:

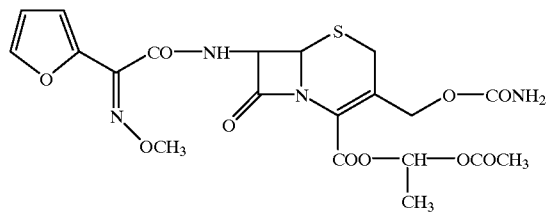

Formula I

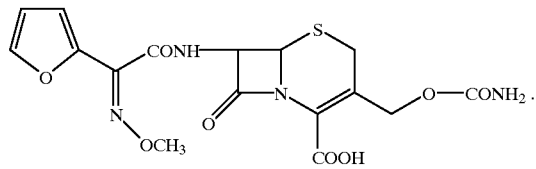

Formula II

2. The process as claimed in claim 1, wherein after the reaction of cefuroxime axetil and alkoxide is complete, the reaction mixture is acidified, the solvent is removed under reduced pressure, water is added to the reaction mixture and the cefuroxime is extracted with a water-immiscible solvent by adding a basifying agent, separating the aqueous layer and precipitating cefuroxime therefrom by acidification.

3. The process as claimed in claim 2 wherein the basifying agent is alkali bicarbonate.

4. The process a claimed in claims 1 or 2 wherein cefuroxime axetil is treated with said alkoxide in the presence of said solvent or solvent mixture at a temperature ranging from −80 to +40° C.

5. The process as claimed in claim 1 wherein alkoxide is alkali alkoxide.

6. The process as claimed in claim 5 wherein alkali alkoxide is sodium alkoxide.

7. The process as claimed in claim 6 wherein sodium alkoxide is sodium methoxide or sodium ethoxide.

8. The process as claimed in claim 1 wherein a suitable solvent(s) is selected from the group consisting of a lower alkanol, a non-alcoholic polar solvent and mixtures thereof.

9. The process as claimed in claim 8 wherein said lower alkanol comprises primary, secondary and tertiary alcohols having from 1 to 6 carbon atoms.

10. The process as claimed in claim 9 wherein lower alkanol is methyl, ethyl or isopropyl alcohol.

11. The process as claimed in claim 8 wherein non-alcoholic polar solvent comprises tetrahydrofuran, 1,4-dioxane, N,N-dimethylformamide or dimethylsulfoxide.

12. The process as claimed in claim 2 wherein said water-immiscible solvent is selected from the group consisting of ethyl acetate, isopropyl acetate, diethyl ether, dichloromethane and mixtures thereof.

13. The process as claimed in claim 3 wherein the alkali bicarbonate is potassium bicarbonate.

* * * * *